(12) United States Patent
Chattopadhyay et al.

(10) Patent No.: US 6,676,976 B2
(45) Date of Patent: Jan. 13, 2004

(54) PROCESS FOR THE PRODUCTION OF VASICINE

(75) Inventors: Sunil Kumar Chattopadhyay, Uttar Pradesh (IN); Guru Das Bagchi, Uttar Pradesh (IN); Prem Dutt Dwivedi, Uttar Pradesh (IN); Sachin Srivastava, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/104,765

(22) Filed: Mar. 21, 2002

(65) Prior Publication Data

US 2003/0180392 A1 Sep. 25, 2003

(51) Int. Cl.$^7$ .............................................. A61K 35/78
(52) U.S. Cl. ........................ 424/725; 424/774; 514/247
(58) Field of Search ................................ 424/725, 774; 514/247

(56) References Cited

PUBLICATIONS

Chowdhury et al. (Phytochemistry (1985), vol. 24, No. 12, pp. 3080–3082).*

* cited by examiner

*Primary Examiner*—Leon B. Lankford, Jr.
*Assistant Examiner*—Susan D. Coe
(74) *Attorney, Agent, or Firm*—John P. White; Cooper & Dunham LLP

(57) ABSTRACT

The present invention relates to an improved process for the production of vasicine of formula (1) from the *Adhatoda vasica,* said process comprising the steps of:

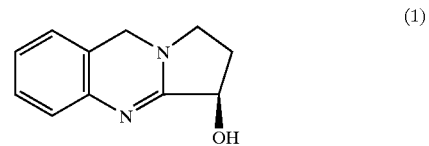

(1)

extracting the dried and pulverized leaves with an alcoholic extract at an ambient temperature, concentrating the alcoholic extract to obtain a concentrated extract, treating and stirring extract with an aqueous organic acid for 2–24 hours, extracting the acid solution of with an organic solvent, separating the organic layer and aqueous acidic layer, basifying the aqueous acidic solution with a base, extracting the basified solution with an organic solvent, separating the organic layer, drying and filtering, evaporating the organic layer to obtain an amorphous residue, and treating the amorphous residue with an organic solvent or mixture of organic solvents to obtain vasicine.

15 Claims, No Drawings

PROCESS FOR THE PRODUCTION OF VASICINE

Throughout this application various publications are referred to by author(s) and year within parenthesis. The disclosures of these publications, in their entireties, are hereby incorporated by reference into this application in order to more fully describe the state of art to which the invention pertains.

FIELD OF INVENTION

This invention relates to an improved process for the production of vasicine. More particularly, this invention relates to a process for the production of a biologically active compound vasicine of formula (1) from the leaves of *Adhatoda vasica*.

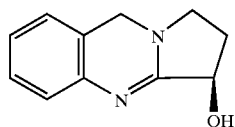

(1)

BACKGROUND OF INVENTION

*Adhatoda vasica* belonging to the family Acanthaceae is commonly known as 'Arusa', 'Vasaka' or 'Malabarnut'. It is an evergreen and perennial shrub and attains a height up to 2.0 m at north Indian plain conditions. The plant is a well-known drug of Ayurvedic system of medicine. In India, it has been used for over 2000 years for the treatment of respiratory complaints and diseases like coughing, asthma and colds. The most studied chemical component of the plant is vasicine. It showed bronchodialatory activity both in vitro and in vivo comparable to theophylline. It was also observed that vasicine initiated rhythmic contractions of human myometrial strips from both non-pregnant and pregnant uteri. The effect was comparable with that of oxytocin and methergin (C.K. Atal.Chemistry and Pharmacology of vasicine—a new oxytocic and abortifacient. Raj. Bandhu Ind. Co., New Delhi, 1980).

According to a prior art process vasicine can be isolated from the leaves of *A.vasica* by extracting the leaves of the plant with 95% alcohol, treating the concentrated alcoholic extract with aqueous 2% $H_2SO_4$, basifying the aqueous acidic solution with ammonia and extracting with chloroform, concentrating the chloroform gave a extract which was again dissolved in aqueous 2% $H_2SO_4$ and repeating the process of basification with ammonia, followed by extraction with chloroform (C.K.Atal. Chemistry and Pharmacology of vasicine—a new oxytocic and abortifacient. Raj. Bandhu Ind. Co., New Delhi, 1980). The drawback of the process include use of strong mineral acid like $H_2SO_4$ for extraction which result in considerable degradation of vasicine, which is further aggravated by repeating the process of same mineral acid treatment twice.

In another prior art, process vasicine was isolated from *A.vasica* leaves as follows (D. R. Mehta, J. S. Naravane and R. M. Desai. J. Org. chem. 28, 445–448, 1963). The leaves were refluxed with 90% alcohol and after evaporation of the solvent the alcohol extract thus obtained was extracted with hot distilled water and the aqueous extract was filtered. The filtrate was extracted with chloroform to remove the coloring matters and then made alkaline with 5% caustic soda, and again extracted with chloroform. The combined chloroform extracts were extracted with 5% hydrochloric acid, then acidic solution was made alkaline with ammonia and again extracted with chloroform.

After repeating the process twice the final chloroform extract was concentrated to give a crude total alkaloid from which vasicine was isolated as vasicine hydrochloride yield 2 g. The first drawback of the above process includes the extraction of the alcohol extract with hot water, which has two drawbacks—viz, (a) vasicine could not be quantitatively extracted from its aqueous solution and (b) hot water extraction will convert vasicine into its auto oxidation product vasicinone.

Second drawback of the process is the use of 5% mineral acid like hydrochloric acid for its extraction and that also, twice. The use of a strong mineral acid degrades vasicine considerably and thus results in a lower yield of vasicine.

OBJECTS OF THE INVENTION

The object of the present invention is to develop an improved process for isolation of vasicine of formula (1) from the leaves of the plant *A.vasica* with high yields.

Another object of the present invention is to develop a processing technology for its isolation, which does not use any chromatographic separation for its isolation. Still another object of the present invention is to develop a processing technology for isolation of vasicine, which can be applicable to commercial scale production of this important molecule.

SUMMARY OF INVENTION

Accordingly, in order to overcome the drawbacks of the prior art processes, the applicants have developed a simple and practical process adaptable to commercial production of vasicine. The process comprises (a) extracting air dried, pulverized leaves of *Adhatoda vasica* with alcohol at room temperature, evaporating the solvent to obtain an alcoholic extract, (b) stirring the resultant residue with aqueous solution of an organic acid for 2–24 hours and (c) extracting the acidic layer with organic solvent, (d) basifying the aqueous acidic solution with a suitable base and extracting the basic layer with organic solvent exhaustively and concentrating the organic phase gave a semi solid residue of vasicine, (d) isolating vasicine from the resultant residue by treating it with a suitable solvent or mixture of solvents and filtering.

DETAILED DESCRIPTION OF THE PROCESS

Accordingly, the present invention provides an improved process for the production of vasicine of formula (1) from the *Adhatoda vasica*, said process comprising the steps of:

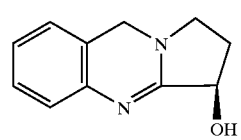

(1)

a. extracting the dried and pulverized leaves with an alcoholic extract at an ambient temperature,
b. concentrating the alcoholic extract of step (a) to obtain a concentrated extract,
c. treating and stirring extract of step (b) with an aqueous organic acid for 2–24 hours.
d. extracting the acid solution of steps (c) with an organic solvent, e. separating the organic layer and aqueous acidic layer of step (d), f. basifying the aqueous acidic solution of step (e) with a base, g. extracting the basified solution of step (f) with an organic solvent, h. separating the organic layer of step (g) drying and filtering, i. evaporating the organic layer of step (h) to obtain an amorphous residue, and j. treating the amorphous residue of step (i) with an organic solvent or mixture of organic solvents to obtain vasicine.

In an embodiment of the invention, in step (a and b) the alcohol used is selected from a group consisting of methanol, ethanol, propanol, n-butanol and preferably methanol and ethanol.

Still another embodiment of the invention, in step (c) the organic acid used is selected from group consisting of citric acid, oxalic acid, tartaric acid, acetic acid or propionic acid.

Still another embodiment of the invention relates to the use of organic acid in step (c), which is preferably citric acid.

Yet another embodiment of the invention, the organic solvent used in step (d) is selected from the group consisting of chloroform, dichloromethane, ether, ethyl acetate, toluene and more preferably chloroform and most preferably dichloromethane.

Yet another embodiment of the invention, the base used in step (f) is selected from a group consisting of aqueous ammonia, sodium hydroxide, sodium carbonate, potassium carbonate, lithium hydroxide and preferably aqueous ammonia.

Yet another embodiment of the invention, the organic solvent used in step (g) is selected from a group consisting chloroform, dichloromethane, ether, ethyl acetate, toluene more preferably dichloromethane and most preferably chloroform.

Yet another embodiment of the invention, the solvent used to obtain vasicine in step (j) is selected from a group consisting of acetone, ether, petroleum ether and/or mixture thereof.

Yet another embodiment of the invention, the preferred solvent used in step (j) is a mixture of petroleum ether-acetone in the ratio 1:1 to 2:1.

Yet another embodiment of the invention, the vasicine obtained has a minimum purity of 80%.

Yet another embodiment of the invention, the recovery of vasicine obtained by this process is 2.0%, which is not obtained so far by any methods reported.

Yet another embodiment the vasicine is quantitatively extracted from the raw material.

Yet, another embodiment of the invention relates to a process, wherein the said process can be applied for isolation of vasicine irrespective of plant species.

In yet another embodiment of the invention depending upon the source of the plant material, the purity of the vasicine is affected.

The invention is described in detail in the examples given below which are provided to illustrate the invention and therefore should not be construed to limit the scope of the invention.

EXAMPLE I

Air-dried, powdered leaf of A.vasica (1 Kg.) was extracted with methanol (3 liters×5) at 20–40° C. for seventy-two hours. The combined methanol extract was concentrated under reduced pressure to give a concentrated extract (200 ml). The said extract was then treated with a aqueous solution of citric acid (1.0 liter) and was stirred at ambient temperature for 2–24 hours. It was filtered and the clear solution thus obtained was extracted with chloroform (1.0 liter×3). The aqueous acidic layer was then basified with ammonia solution to pH 9.5 and the basic aqueous solution was extracted with chloroform (1 liter×3) and the chloroform extract was concentrated under reduced pressure to give an amorphous residue of vasicine; the amorphous residue thus obtained was triturated with a mixture of acetone-petroleum ether (Ratio of pet.ether:acetone 1:1; 100 ml) with stirring and filtered to give vasicine (20 gms) with 80% purity

EXAMPLE II

An air-dried, powdered leaf of A.vasica (1 Kg) was extracted with ethanol (3 liter×5) under the same condition described above to give a concentrated extract (200 ml). The said extract was then treated with a aqueous solution of tartaric acid (1.0 liter) and was stirred at ambient temperature for 2–24 hours. The acidic solution after filtration was extracted with dichloromethane (1.0 liter×3); then the said acidic solution was basified with aqueous solution of sodium carbonate and was extracted with dichloromethane (1liter× 3). The dichloromethane extract after concentration gave amorphous vasicine, which was then treated with ether—petroleum ether mixture in the ratio of petroleum ether:acetone 2:1, with stirring and filtered to give vasicine (20 g) with 84% purity

ADVANTAGES (1) No chromatographic separation is needed at any stage for isolation of vasicine. Thus, the process described is cost effective and adaptable for large-scale production of vasicine.

(2) The process described for isolation of vasicine involves normal condition of temperature and pressure. Thus, the process is simple, straightforward and adaptable to commercial production.

(3) The recovery of vasicine obtained by this process is 2.0%, which is not obtained so far by any methods reported.

(4) The process can be applied for isolation of vasicine irrespective of plant species. Thus the process described here, is a general process for isolation of vasicine.

What is claimed is:

1. A process for the production of vasicine of formula (1) from the *Adhatoda vasica,* wherein no chromatographic separation is used, said process comprising the steps of:

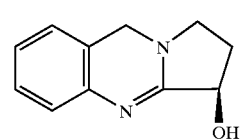

(1)

a. extracting the dried and pulverized leaves with an alcoholic extract at an ambient temperature, b. concentrating the alcoholic extract of step (a) to obtain a concentrated extract, c. treating and stirring extract of step (b) with an aqueous organic acid for 2–24 hours, d. extracting the acid solution of steps (c) with an organic solvent, e. separating the organic layer and aqueous acidic layer of step (d), f. basifying the aqueous acidic solution of step (e) with a base, g. extracting the basified solution of step (f) with an organic solvent, h. separating the organic layer of step (g) drying and filtering, i. evaporating the organic layer of step (h) to obtain an amorphous residue, and j. treating the amorphous residue of step (i) with a mixture of petroleum ether-acetone in the ratio of 1:1 to 2:1 to obtain vasicine that has a minimum purity of 80%.

2. A process as claimed in claim 1, wherein in step (a) the alcohol used is selected from a group consisting of methanol, ethanol, propanol, n-butanol.

3. A process as claimed in claim 1, wherein in step (c) the organic acid used is selected from group consisting of critic acid, oxalic acid, tartaric acid, acetic acid or propionic acid.

4. A process as claimed in claim 1, wherein in step (c) the preferred organic acid is citric acid.

5. A process as claimed in claim 1, wherein in step (d) the organic solvent used is selected from the group consisting of chloroform, dichloromethane, ether, ethyl acetate, and toluene.

6. A process as claimed in claim 1, wherein in step (f) the base used is selected from a group consisting of aqueous ammonia, sodium hydroxide, sodium carbonate, potassium carbonate, and lithium hydroxide.

7. A process as claimed in claim 1, wherein in step (g) the organic solvent used is selected from a group consisting of chloroform, dichloromethane, ether, ethyl acetate, and toluene.

8. A process as claimed in claim 1, wherein in step (j) the solvent used to obtain vasicine is selected from a group consisting of acetone, ether, petroleum ether and/or mixture thereof.

9. A process as claimed in claim 1, wherein the vasicine is quantitatively extracted from said amorphous residue.

10. A process as claimed in claim 2, wherein the alcohol used is methanol or ethanol.

11. A process as claimed in claim 5, wherein the organic solvent used is chloroform.

12. A process as claimed in claim 5, wherein the organic solvent used is dichloromethane.

13. A process as claimed in claim 6, wherein the base used is aqueous ammonia.

14. A process as claimed in claim 7, wherein the organic solvent used is chloroform.

15. A process as claimed in claim 7, wherein the organic solvent used is dichloromethane.

* * * * *